United States Patent
Pruche et al.

(10) Patent No.: US 6,409,772 B2
(45) Date of Patent: *Jun. 25, 2002

(54) USE OF HYDROXYSTILBENES FOR DYEING, READY-TO-USE COMPOSITION CONTAINING THEM AND DYEING PROCESS

(75) Inventors: Francis Pruche, Paris; Didier Saint Leger, Courbevoie; Bruno Bernard, Neuilly S/Seine, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/467,896

(22) Filed: Dec. 21, 1999

(30) Foreign Application Priority Data

Dec. 22, 1998 (FR) .......................................... 98 16258

(51) Int. Cl.$^7$ ................................................ A61K 7/13
(52) U.S. Cl. ........................ 8/406; 8/407; 8/408; 8/424; 8/646; 8/648; 8/649
(58) Field of Search ............................ 8/406, 407, 408, 8/424, 646, 648, 649; 568/729, 744, 745

(56) References Cited

U.S. PATENT DOCUMENTS

| | | | |
|---|---|---|---|
| 3,406,194 A | 10/1968 | Simon et al. | 260/479 |
| 4,182,612 A | 1/1980 | Sokol et al. | 8/405 |

FOREIGN PATENT DOCUMENTS

| | | |
|---|---|---|
| CH | 578 645 | 8/1976 |
| EP | 0 270 972 | 6/1988 |
| FR | 2 777 184 | 10/1999 |
| WO | WO 99 03816 A | 1/1999 |
| WO | WO 99 04747 A | 2/1999 |

OTHER PUBLICATIONS

CAPLUS Abstract of Donnelly et al, "Enzyme–mediated hydrogen eproxide oxidation of (E)–stilbene–3,4–diol," J. Chem. Soc. (12), 2719–22, 1987.*

CAPLUS Abstract of Morales et al, "Oxidation of trans–resveratorl by a hypodermal peroxidase isoenzyme from Gamay rouge grape (*Vitis vinifera*) berries," Am. J. Enol. Vitic. 48(1), 33–38, 1987.*

Derwent Publications Ltd., AN 89–088653 "Skin whitening cosmetic material—contains hydroxystilbene cpds" & JP 01 038009 A, Feb. 8, 1989.

Derwent Publications Ltd., AN 96–368079, "Cosmetic contg. Stilbene deriv.—used for preventing wrinkles formation on skin due to UV light exposure" and JP 08 175960, Jul. 9, 1996.

Chemical Abstracts, vol. 114, No. 18, May 6, 1991, Huang et al, Hair growth stimulating preparations containing medicinal plant extracts, p. 430.

* cited by examiner

*Primary Examiner*—John Hardee
(74) *Attorney, Agent, or Firm*—Nixon & Vanderhye P.C.

(57) ABSTRACT

The invention relates to the use of hydroxystilbenes for dyeing, to ready-to-use dye compositions comprising them, to a dyeing process using them and to a multi-compartment device containing the compositions used in the processes of the invention.

19 Claims, No Drawings

USE OF HYDROXYSTILBENES FOR DYEING, READY-TO-USE COMPOSITION CONTAINING THEM AND DYEING PROCESS

The present invention relates to the use of hydroxystilbenes, to ready-to-use dye compositions containing them, to dyeing processes using them and to a multi-compartment device used for carrying out the said dyeing processes.

It is well known to use so-called "oxidation" dyes in compositions for dyeing the hair. These dyes have the advantage of leading to shades which give better coverage and which are faster than those obtained using so-called "direct" dyes. Nevertheless, the oxidation dyes currently used have the drawback of not being entirely harmless and thus entail potential risks of allergies.

The Applicant has investigated oxidation dyes which do not have these drawbacks and which give the hair a coloration with satisfactory resistance to light, washing, bad weather, perspiration and various treatments to which the hair may be subjected. Furthermore, oxidizing dyes are also sought which can be used in the context of enzymatic colorations and which can thus make it possible to avoid the use of oxidizing agents such as hydrogen peroxide, which can be the cause of substantial degradation of keratin fibres.

Japanese patent application No. 64-38009 describes the use of hydroxystilbenes as tyrosinase inhibitors and discloses depigmenting compositions containing hydroxystilbenes.

The Applicant has just discovered, and this forms the subject of the invention, that the use of hydroxystilbenes as oxidation dye precursors in dye compositions makes it possible to obtain a wide range of colorations, the said colorations having particularly noteworthy resistance to light, washing, bad weather and perspiration.

One subject of the invention is thus the use of hydroxystilbene for dyeing, and particularly for dyeing keratin substances.

Another subject of the invention consists of ready-to-use dye compositions containing at least one hydroxystilbene and an oxidizing agent.

Another subject of the invention also relates to a process for dyeing a support, and in particular keratin substances, using such compositions.

Another subject of the invention relates to a multi-compartment dyeing device or kit containing the various compounds used for the dyeing operations according to the invention for dyeing.

An essential subject of the present invention is thus the use of hydroxystilbene of formula (I) below:

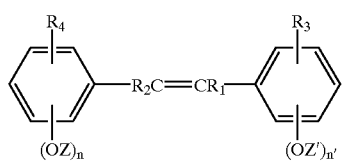

in which:
n denotes an integer from 2 to 4,
n' denotes an integer from 0 to 4,
$R_1$ and $R_2$, which may be identical or different, denote a hydrogen atom, a halogen atom or an alkyl, alkoxy, carboxyl or acyl radical;
$R_3$ and $R_4$, which may be identical or different, denote a hydrogen atom, a halogen atom or an alkyl, alkoxy, carboxyl or acyl radical;
Z and Z', which may be identical or different, represent a hydrogen atom or a glycosyl radical.

In formula (I) above, the alkyl, alkoxy or acyl radicals may be linear or branched.

The alkyl groups in particular denote groups of 1 to 20 carbon atoms such as, for example, ethyl, methyl, propyl, isopropyl, n-propyl, butyl, n-butyl, tert-butyl, pentyl, n-pentyl, isopentyl, n-hexyl, isohexyl, octyl, nonyl, decyl, undecyl and pentadecyl groups. Preferably, these alkyl groups denote a group of 1 to 6 carbon atoms.

The alkoxy groups denote groups —O—R, R representing an alkyl group as defined above.

The acyl groups denote groups —COR, R representing an alkyl group as defined above.

The glycosyl radical represents a radical derived from a glycose, i.e. a monosaccharide or simple sugar, such as arabinose, glucose or fructose. The glycosyl radical preferably denotes a glucosyl radical.

The hydroxystilbenes of formula (I) can be used for dyeing supports of very varied nature, such as cotton, cellulose, plastics, etc. Specifically, it has been found that the use of these dye precursors makes it possible to obtain dyes which have a strong affinity for their support.

In one preferred embodiment of the invention, the hydroxystilbenes are used for dyeing keratin substances such as the skin or keratin fibres such as the hair or the nails.

In one preferred embodiment of the invention, the compounds of formula (I) are chosen from those for which $R_1$ and $R_2$ denote a hydrogen atom and $R_3$ and $R_4$, which may be identical or different, denote a hydrogen atom or a $C_1$-$C_4$ alkyl, $C_1$-$C_4$ alkoxy or carboxyl radical.

Even more preferably, the hydroxystilbenes of formula (I) are chosen from the following compounds:
4'-methoxy-3,3',5-stilbenetriol 3-glucoside or rhapontin,
trans-1-(3'-carboxy-4'-hydroxyphenyl)-2-(2',5'-dihydroxyphenyl)ethane,
3,5-dihydroxy-4'-methoxystilbene 3-O-beta-D-glucoside or deoxyrhapontin,
trans-3,4',5-trihydroxystilbene or resveratrol,
4',5-dihydroxystilbene 3-O-beta-D-glucoside,
3,3',4,5'-tetrahydroxystilbene or picestannol,
3,5-dihydroxy-4'-bromostilbene,
3,5,3'-trihydroxy-4'-methoxystilbene 5-O-beta-D-glucoside;
or one of the addition salts thereof with an acid.

Another subject of the invention relates to ready-to-use dye compositions comprising, in a medium which is suitable for dyeing, at least one compound of formula (I) as defined above and at least one oxidizing agent.

The oxidizing agent may be chosen in particular from enzymes, hydrogen peroxide, urea peroxide, persalts and peracids, metal salts such as, for example, copper salts, quinones and nitrites.

The enzymes can be chosen in particular from pyranose oxidases, glucose oxidases, glycerol oxidases, lactate oxidases, pyruvate oxidases, uricases, choline oxidases, sarcosine oxidases, bilirubin oxidases, laccases, tyrosinases, peroxidases and catalases, or from plant or animal extracts containing the abovementioned enzymes, optionally in the presence of a donor (or substrate) required for the functioning of the said enzymes.

When the enzymes are used as oxidizing agents, and in particular tyrosinase, the ready-to-use dye compositions of the invention can thus also contain L-tyrosine; pyrimidine 3-oxide derivatives substituted in position 6, in particular those described in FR 96/11316, L-DOPA; dopamine; peptides with L-tyrosine, L-DOPA and/or dopamine residues; caffeic acid; coumaric acid; chlorogenic acid; elagic acid;

catechins; OPCs or plant or animal extracts containing these abovementioned compounds.

The enzymes used according to the invention can be of animal, microbiological (bacterial, fungal or viral) or synthetic (obtained by chemical or biotechnological synthesis) origin.

The enzyme(s) can be used in pure crystalline form or in diluted form in a diluent which is inert with respect to the said enzyme.

Examples of uricases which may be mentioned in particular are uricase extracted from boar liver, uricase from *Arthrobacter globiformis* and uricase from *Aspergillus flavus*.

Examples of sources of choline oxidase which may be mentioned in particular are rat liver, bacteria such as *Arthrobacter globiformis, Achromobacter cholinophagum* or Alcaligenes, and fungi such as *Cylindrocarpon didynum*.

Examples of sources of sarcosine oxidase which may be mentioned in particular are bacteria such as Arthrobacter and in particular *Arthrobacter ureafaciens* and *Arthrobacter globiformis*, Streptomyces, Bacillus, Pseudomonas, Corynebacterium or Alcaligenes such as, for example, *Alcaligenes denitrificans*, and fungi such as *Cylindrocarpon didynum*.

Examples of sources of bilirubin oxidase which may be mentioned in particular are intestinal mucosa and rat liver, and bacteria such as *Myrothecium verucania, Myrothecium cinctum* and *Myrothecium roridum*.

Among the laccases of plant origin which can be used according to the invention, mention may be made of the laccases produced by plants which synthesize chlorophyll, such as those indicated in patent application FR-A-2,694,018.

Mention may be made in particular of the laccases extracted from Anacardiacea plants, from Podocarpacea plants, from *Rosmarinus off.*, from *Solanum tuberosum*, from Iris sp., from Coffea sp., from *Daucus carrota*, from *Vinca minor*, from *Persea americana*, from *Catharenthus roseus*, from Musa sp., from *Malus pumila*, from *Gingko biloba* and from *Monotropa hypopithys* (Indian pine).

Among the laccases of microbial (in particular fungal) origin, or obtained by biotechnology, which can be used according to the invention, mention may be made of the laccases from *Polyporus versicolor*, from *Rhizoctonia praticola* and from *Rhus vernicifera*, as described, for example, in patent applications FR-A-2,112,549 and EP-A-504,005; the laccases described in patent applications WO95/07988, WO95/33836, WO95/33837, WO96/00290, WO97/19998 and WO97/19999, the content of which forms an integral part of the present description, such as, for example, the laccases of Scytalidium, of *Polyporus pinsitus*, of *Myceliophthora thermophila*, of *Rhizoctonia solani*, of *Pyricularia oryzae* and variants thereof.

Laccases of microbial origin or those obtained by biotechnology will be chosen more preferably.

In one particularly preferred embodiment of the invention, the enzyme used corresponds to tyrosinase. In the present invention, the term "tyrosinase" should be understood as meaning any enzyme with tyrosinase activity, it being possible for this enzyme to have other enzymatic activities. Tyrosinase activity can be defined as the enzymatic activity which catalyses the oxidation of tyrosinase to lead to the formation of the melanin precursor: dopaquinone.

Examples of sources of tyrosinase which may be mentioned in particular are potato, mushrooms, microorganisms such as *Neurospora crassa*, etc.

In the ready-to-use compositions according to the invention, the compound(s) of formula (I) represent(s) from 0.01 to 10% by weight relative to the total weight of the ready-to-use dye composition and preferably from 0.1 to 5% by weight relative to the total weight of the ready-to-use dye composition.

The oxidizing agent itself can represent from 0.001 to 25% by weight relative to the total weight of the ready-to-use dye composition and preferably from 0.1 to 10% by weight relative to the total weight of the ready-to-use dye composition.

The ready-to-use dye composition in accordance with the invention can also contain one or more oxidation dye precursors other than those of formula (I), i.e. one or more oxidation bases and/or one or more couplers.

When they are present, the oxidation base(s) preferably represent(s) from 0.0005 to 12% by weight approximately relative to the total weight of the ready-to-use dye composition in accordance with the invention and even more preferably from 0.005 to 8% by weight approximately relative to this weight.

When they are present, the coupler(s) preferably represent(s) from 0.0001 to 10% by weight approximately relative to the total weight of the ready-to-use dye composition and even more preferably from 0.005 to 8% by weight approximately relative to this weight.

The ready-to-use dye composition according to the invention can also contain one or more direct dyes which can be chosen in particular from azo dyes, anthraquinone dyes and nitro derivatives of the benzene series, in particular to modify the shades or to enrich them with glints.

When the compositions of the invention are used for dyeing the skin, they can also contain DHA.

The medium which is suitable for dyeing generally consists of water or a mixture of water and at least one organic solvent to dissolve the compounds which would not be sufficiently soluble in water.

The solvents can be present in proportions preferably of between 1 and 40% by weight approximately relative to the total weight of the dye composition and even more preferably between 5 and 30% by weight approximately.

The pH of the ready-to-use compositions of the invention may be adapted as a function of the oxidizing agent used and such that the dyeing properties of the composition are not adversely affected. The pH values will, in particular, have to be adapted so as not to denature the enzymes when they are used as oxidizing agents. Thus, the compositions of the present invention may have a pH of between 3 and 12 and preferably a pH of less than 8.

This pH can be adjusted to the desired value by means of acidifying or basifying agents usually used for dyeing.

The dye composition in accordance with the invention can also contain various adjuvants conventionally used in compositions for dyeing, and in particular for dyeing the hair, such as surfactants, polymers, inorganic or organic thickeners, anti-oxidants, penetrating agents, sequestering agents, fragrances, buffers, dispersants or conditioning agents.

Needless to say, a person skilled in the art will take care to select this or these optional additional compounds mentioned above such that the advantageous properties intrinsically associated with the dye composition in accordance with the invention are not, or are not substantially, adversely affected by the addition or additions envisaged.

The ready-to-use dye composition according to the invention can be in various forms, such as in the form of liquids, creams or gels or in any other form which is suitable for dyeing, and in particular dyeing keratin substances.

Another subject of the invention relates to a dyeing process in which at least one dye composition as defined above is applied to a support for a period which is sufficient to develop the desired coloration.

Preferably, the support used in this dyeing process consists of keratin substances. In this case, the time required to develop the coloration may be from about 1 minute to 1 hour and more specifically from 5 to 40 minutes. After this application to the keratin substances, they are rinsed, optionally washed with shampoo, rinsed again and dried.

In another embodiment of the process of the invention, the said process comprises a preliminary step which consists in separately storing, on the one hand, a composition (A) comprising, in a medium which is suitable for dyeing, at least one compound of formula (I) as defined above, and, on the other hand, a composition (B) containing, in a medium which is suitable for dyeing, at least one oxidizing agent as defined above, and then in mixing them together at the time of use, after which this mixture is applied to the support.

The present invention also relates to a multi-compartment dyeing device or "kit" comprising a first compartment containing the composition (A) defined above and a second compartment containing the composition (B) defined above.

When the oxidizing agent of composition (B) corresponds to an enzyme, this enzyme can be in the form of powder or immobilized, i.e. bound to a matrix.

These devices can be equipped with a means for applying the desired mixture to the hair, such as the devices described in patent FR 2,586,913.

The examples which follow are intended to illustrate the invention without, however, limiting its scope.

The dye compositions below, in accordance with the invention, were prepared:

| Example | 1 | 2 | 3 | 4 |
|---|---|---|---|---|
| Resveratrol (compound of formula (I)) | 5.26 mmol | 5.26 mmol | 5.26 mmol | 5.26 mmol |
| 5,6-Dihydroxyindoline | — | 0.173 mmol | — | — |
| 2,4-Diaminophenoxyethanol dihydrochloride | — | — | 0.173 mmol | — |
| 5,6-Dihydroxyindole | — | — | — | 0.173 mmol |
| Caffeic acid | 0.173 mmol | — | — | — |
| Laccase | 0.002 g | 0.002 g | 0.002 g | 0.002 g |
| Phosphate buffer pH 7.2 qs | 100 ml | 100 ml | 100 ml | 100 ml |

| Example | 5 | 6 | 7 | 8 | 9 |
|---|---|---|---|---|---|
| Resveratrol (compound of formula (I)) | 5.26 mmol | 5.26 mmol | 5.26 mmol | 5.26 mmol | 5.26 mmol |
| 2,4-Diaminophenoxyethanol dihydrochloride | — | — | — | 0.173 mmol | — |
| 5,6-Dihydroxyindole | — | — | — | — | 0.173 mmol |
| Paraphenylenediamine | 0.173 mmol | — | — | — | — |
| Caffeic acid | — | — | 0.173 mmol | — | — |
| Laccase | 0.002 g | — | — | — | — |
| Tyrosinase | — | 0.068 g | 0.068 g | 0.068 g | 0.068 g |
| Phosphate buffer pH 7.2 qs | 100 ml | 100 ml | 100 ml | 100 ml | 100 ml |

Each of the above dye compositions was applied to locks of natural grey hair containing 90% white hairs for 30 minutes at 37° C.

The locks were then rinsed, washed with shampoo, rinsed again and then dried.

The hair was dyed in a shade given in the table below:

| EXAMPLE | SHADE OBTAINED |
|---|---|
| 1 | Very light golden blond |
| 2 | Light ash blond |
| 3 | Slightly matt light ash blond |
| 4 | Matt slightly golden light ash blond |
| 5 | Slightly golden matt blond |
| 6 | Light golden blond |
| 7 | Light golden blond |
| 8 | Slightly matt very light ash blond |
| 9 | Ash blond |

What is claimed is:

1. Ready-to-use dye composition, characterized in that it comprises, in a medium which is suitable for dyeing, from 0.01 to 10% by weight relative to the total weight of the ready-to-use dye composition, of at least one compound of formula (I):

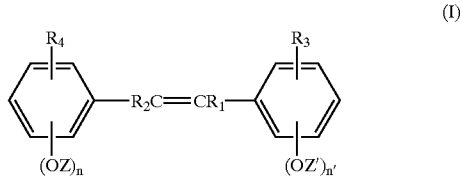

in which:

n denotes an integer from 2 to 4, n' denotes an integer from 0 to 4, $R_1$ and $R_2$, which may be identical or different, denote a hydrogen atom, a halogen atom or an alkyl, alkoxy, carboxyl or acyl radical;

$R_3$ and $R_4$, which may be identical or different, denote a hydrogen atom, a halogen atom or an alkyl, alkoxy, carboxyl or acyl radical;

Z and Z', which may be identical or different, denote a hydrogen atom or a glycosyl radical; and at least one oxidizing agent chosen from hydrogen peroxide, urea peroxide, persalts and peracids, copper salts, quinones and nitrites, pyranose oxidases, glucose oxidases, glycerol oxidases, lactate oxidases, pyruvate oxidases, uricases, choline oxidases, laccases, sarcosine oxidases, bilirubin oxidases, tyrosinases, peroxidases and catalases, or from plant or animal extracts containing the above-mentioned enzymes, optionally in the presence of a donor required for the functioning of the said enzymes.

2. Ready-to-use dye composition according to claim 1, characterized in that $R_1$ and $R_2$ denote a hydrogen atom and $R_3$ and $R_4$, which may be identical or different, denote a hydrogen atom or a $C_1$-$C_4$ alkyl, $C_1$-$C_4$ alkoxy or carboxyl radical.

3. Ready-to-use dye composition according to claim 1, characterized in that the compounds of formula (I) are chosen from the following compounds:

4'-methoxy-3,3',5-stilbenetriol-3-glucoside, trans-1-(3'-carboxy-4'-hydroxyphenyl)-2-(2",5"-dihydroxyphenyl)-ethane, 3,5-dihydroxy-4'-methoxystilbene 3-O-beta-D-glucoside, trans-3,4',5-trihydroxystilbene, 4',5-dihydroxystilbene 3-O-beta-D-glucoside, 3,3',4,5'-tetrahydroxystilbene, 3,5-dihydroxy-4'-bromostilbene, 2,3,5,4'-tetrahydroxystilbene 2-O-beta-D-glucoside, and 3,5,3'-trihydroxy-4'-methoxystilbene 5-O-beta-D-glucoside.

4. Ready-to-use dye composition according to claim 1, characterized in that the oxidizing agent is tyronsinase.

5. Ready-to-use dye composition according to claim 4, characterized in that it also contains L-tyrosine; a pyrimidine 3-oxide derivative substituted in position 6; L-DOPA; dopamine; peptides with L-tyrosine, L-DOPA and/or dopamine residues; caffeic acid; coumaric acid; chlorogenic acid; elagic acid; catechins; oligomers of procyanidine (OPC) or plant or animal extracts containing these above-mentioned compounds.

6. Ready-to-use dye composition according to claim 1, characterized in that the compound(s) of formula (I) represent(s) from 0.1 to 5% by weight relative to the total weight of the ready-to-use dye composition.

7. Ready-to-use dye compositions according to claim 1, characterized in that the oxidizing agent represents from 0.001 to 25% by weight relative to the total weight of the ready-to-use dye composition.

8. Ready-to-use dye composition according to claim 7, characterized in that the oxidizing agent represents from 0.1 to 10% by weight relative to the total weight of the ready-to-use dye composition.

9. Ready-to-use dye composition according to claim 1, characterized in that it contains one or more oxidation bases other than the compounds of formula (I) and/or one or more couplers.

10. Ready-to-use dye composition according to claim 9, characterized in that the oxidization bass(s) represent(s) from 0.0005 to 12% by weight relative to the total weight of the ready-to-use dye composition and in that the coupler(s) represent(s) from 0.0001 to 10% by weight relative to the total weight of the ready-to-use dye composition.

11. Ready-to-use dye composition according to claim 10, characterized in that the oxidation base(s) represent(s) from 0.005 to 8% by weight relative to the total weight of the dye composition and in that the coupler(s) represent(s) from 0.005 to 8% by weight relative to the total weight of the dye composition.

12. Ready-to-use dye composition according to claim 1, characterized in that it also contains direct and/or self-oxidizing dyes chosen from azo dyes, anthraquinones dyes and nitro derivatives of the benzene series.

13. Ready-to-use dye composition according to claim 1, characterized in that the medium which is suitable for dyeing consists of water or a mixture of water and at least one organic solvent.

14. Ready-to-use dye composition according to claim 1, characterized in that it also contains surfactants, polymers, inroganic or organic thickners, antioxydants, penetrating agents, sequestering agents, fragances, buffers dispersants or conditioning agents.

15. Ready-to-use dye composition according to claim 1, characterized in that it is in the form of liquids, creams or gels, or in any other form which is suitable for carrying out a dyeing operation.

16. Dyeing process, characterized in that at least one dye composition as defined according to claim 1 is applied to a support.

17. Process according to claim 16, characterized in that it comprises a preliminary step comprising separately storing a composition (A) comprising, in a medium which is suitable for dyeing, at least one compound of formula (I) and a composition (B) containing, in a medium which is suitable for dyeing, at least one oxidizing agent, and then mixing them together at of the time of application, after which this mixture is applied to the support.

18. Dyeing process for dyeing keratin substances comprising applying to said keratin substances a compound of formula (I):

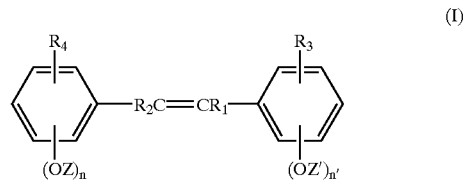

in which:

n denotes an integer from 2 to 4, n' denotes an integer from 0 to 4, $R_1$, and $R_2$, which may be identical or different, denote a hydrogen atom, a halogen atom or an alkyl, alkoxy, carboxyl or acyl radical;

$R_3$ and $R_4$, which may be identical or different, denote a hydrogen atom, a halogen atom or an alkyl, alkoxy, carboxyl or acyl radical;

Z and Z', which may be identical or different, represent a hydrogen atom or a glycosyl radical.

19. Multi-compartment dyeing device or kit, characterized in that it comprises a first compartment containing composition (A) comprising, in a medium which is suitable for dyeing, at least one compound of formula (I):

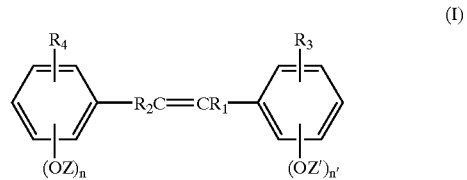

in which:

n denotes an integer from 2 to 4, n' denotes an integer from 0 to 4, $R_1$, and $R_2$, which may be identical or different, denote a hydrogen atom, a halogen atom or an alkyl, alkoxy, carboxyl or acyl radical;

$R_3$ and $R_4$, which may be identical or different, denote a hydrogen atom, a halogen atom or an alkyl, alkoxy, carboxyl or acyl radical;

Z and Z', which may be identical or different, denote a hydrogen atom or a glycosyl radical; and a second compartment containing composition (B) containing, in a medium which is suitable for dyeing, at least one oxidizing agent.

* * * * *